United States Patent
Gorny et al.

(10) Patent No.: US 8,658,420 B2
(45) Date of Patent: Feb. 25, 2014

(54) PHOTOBIOREACTOR FOR ALGAE GROWTH

(75) Inventors: Rudiger Gorny, Oakdale, PA (US);
James P. Mason, Carnegie, PA (US);
Glenn Hilton, Gibsonia, PA (US); Peter Schwarz, Krefeld (DE)

(73) Assignees: Bayer MaterialScience LLC,
Pittsburgh, PA (US); Bayer MaterialScience AG, Leverkusen (DE)

( * ) Notice: Subject to any disclaimer, the term of this patent is extended or adjusted under 35 U.S.C. 154(b) by 533 days.

(21) Appl. No.: 12/559,855

(22) Filed: Sep. 15, 2009

(65) Prior Publication Data

US 2011/0065157 A1    Mar. 17, 2011

(51) Int. Cl.
*C12M 1/00* (2006.01)
*C12M 3/00* (2006.01)
*C12N 1/12* (2006.01)
*F21V 33/00* (2006.01)
*A01G 7/00* (2006.01)
*A01H 13/00* (2006.01)
*A01G 9/00* (2006.01)

(52) U.S. Cl.
USPC .............. 435/292.1; 435/257.1; 362/101; 47/1.4; 47/17

(58) Field of Classification Search
USPC .............. 435/292.1, 292.2, 257.1; 47/1.4, 17; 362/101
See application file for complete search history.

(56) References Cited

U.S. PATENT DOCUMENTS

| | | | |
|---|---|---|---|
| 5,981,271 A | 11/1999 | Doucha et al. | |
| 6,571,735 B1 | 6/2003 | Wilkinson | |
| 2007/0048848 A1* | 3/2007 | Sears | 435/134 |
| 2007/0048859 A1 | 3/2007 | Sears | |
| 2007/0092962 A1 | 4/2007 | Sheppard | |
| 2007/0289206 A1 | 12/2007 | Kertz | |
| 2008/0153080 A1 | 6/2008 | Woods et al. | |
| 2008/0160591 A1 | 7/2008 | Willson et al. | |
| 2008/0311649 A1* | 12/2008 | Cloud et al. | 435/292.1 |
| 2009/0081743 A1 | 3/2009 | Hazelbeck et al. | |
| 2009/0113790 A1 | 5/2009 | Erd | |
| 2009/0203067 A1* | 8/2009 | Eckerle et al. | 435/41 |
| 2010/0028976 A1* | 2/2010 | Hu et al. | 435/257.1 |

FOREIGN PATENT DOCUMENTS

| | | | |
|---|---|---|---|
| WO | 2007098150 A2 | | 8/2007 |
| WO | WO 2007/098150 A2 * | | 8/2007 |
| WO | 2008051865 A2 | | 5/2008 |
| WO | 2009051478 A2 | | 4/2009 |
| WO | 2009051479 A2 | | 4/2009 |
| WO | WO 2009040383 A1 * | | 4/2009 |

* cited by examiner

*Primary Examiner* — Nathan Bowers
*Assistant Examiner* — Lydia Edwards
(74) *Attorney, Agent, or Firm* — John E. Mrozinski, Jr.

(57) ABSTRACT

The present invention provides a flow-through photobioreactor containing at least one thermoplastic multi-wall sheet having an upper layer and a lower layer having arranged there between at least two sidewalls, at least one inner wall and two or more end caps. Also provided is a process for the production of a biofuel with the inventive photobioreactor. The photobioreactor and process of the present invention have the following advantages: genetically engineered microbes that give higher yields cannot escape into the environment, water in the system does not evaporate, no weeding (presence of unwanted algae), UV light from the sun is filtered out by the reactor walls, temperature control is possible, $CO_2$ from power plants, breweries, etc. can be artificially fed to increase yield. The inventive photobioreactor is also less expensive to build than pipe reactors and may have low energy costs to operate, because little or no energy is needed for agitation and pumping in a preferred gravity assisted embodiment.

19 Claims, 4 Drawing Sheets

PHOTOBIOREACTOR FOR ALGAE GROWTH

FIELD OF THE INVENTION

The present invention relates in general to microbe growth and more specifically to a multi-wall thermoplastic, flow-through photobioreactor for cultivation of algae for the production of biofuel.

BACKGROUND OF THE INVENTION

Due to the ever escalating price of petroleum and the increasing competition between foods and other biofuel sources, there is a greater interest in algaculture (farming algae) for making biofuels such as biodiesel, bioethanol, biogasoline, biomethanol, and biobutanol. One proposed benefit from the production of biofuels from algae lies in helping to stabilize the concentration of carbon dioxide in the atmosphere at its present level because during photosynthesis, algae and other photosynthetic organisms capture carbon dioxide and sunlight and convert those into oxygen and biomass.

As those skilled in the art are aware, there are two basic processes used to grow microbes such as algae and/or bacteria, in large amounts e.g. for the biodiesel generation. One process is to use open ponds and the other is to use closed reactors.

The open pond process has the advantages of being easy to build and operate; having low energy costs to operate; providing for easy cleaning of the reactor; and the microbes use $CO_2$ from the environment. However, the open pond method has certain disadvantages including that genetically engineered microbes may not be used due to governmental regulations; water evaporates and thus must be replenished; the microbe culture is susceptible to contamination by other microbes that will result in lower yields; UV light from the sun kills microbes; it is difficult to control the temperature; and artificially feeding microbes with $CO_2$ for higher yields is difficult.

Closed bioreactors have the advantages that genetically engineered microbes that give higher yields cannot escape into the environment, the water in the system does not evaporate, lack of contamination by other microbes, UV light from the sun that kills microbes can be filtered out by the reactor walls, temperature control, although still difficult, can be manageable; and CO, from power plants, breweries, etc. can be artificially fed to increase yield.

Closed bioreactors too have disadvantages, such as being expensive to build; having higher energy costs to operate; bag reactors need less energy than pipe reactors that require the microbe solution to be pumped through the pipes; pipe reactors with high diameters need high turbulent flow to expose all algae to sunlight which results in high energy needs; pipe reactors with high diameters need high wall thicknesses which lowers the light transmission; and $CO_2$ needs to be artificially fed.

Various artisans have attempted to address the deficiencies of bioreactors with differing degrees of success.

Sears, in US Published Patent Application No. 2007/0048859, describes an apparatus and system made of closed bioreactors for aquaculture and harvesting. In certain embodiments, the system of Sears is said to contain bags with various layers, including a thermal barrier layer, which may be used to contain the aquaculture and/or to thermally regulate the temperature of the aquaculture. The system may include various mechanisms for moving fluid within the system, such as a roller type mechanism, and may provide temperature regulation by compartmentalization of the fluid to regulate absorption of solar radiation and/or conductive or emissive heat loss and gain. Sears states that various mechanisms may be used to harvest aquatic organisms grown in the apparatus and process them into commercially useful products, such as biodiesel, methane, animal or human food, substrates for polymer synthesis or other chemical products.

US Published Patent Application No. 2007/0092962 in the name of Sheppard describes a device and method for carbon dioxide sequestering involving the use of a photo-bioreactor with light emitting diodes ("LED's") for the cost-effective photo-fixation of carbon dioxide ($CO_2$). This device and method of Sheppard is said to be useful for removing undesirable carbon dioxide from waste streams.

Kertz, in US Published Patent Application No. 2007/0289206 describes a method and apparatus for sequestering $CO_2$ using algae. The device made of a plurality of vertically suspended bioreactors, each bioreactor being translucent and including a flow channel formed by a plurality of baffles. A culture tank containing a suspension of water and at least one algae and including a plurality of gas jets for introducing a $CO_2$ containing gas into the suspension. The culture tank is in fluid communication with an inlet in each channel for flowing the suspension through the channel in the presence of light. A pump pumps the suspension into the channel inlet.

Woods et al., in US Published Patent Application No. 2008/0153080, detail a device for growing genetically enhanced aquatic photoautotrophic organisms in a stable culture, causing the organisms to produce ethanol, and then separating, collecting, and removing the ethanol in situ.

US Published Patent Application No. 2008/0160591 in the name of Wilson et al., describes a scalable photobioreactor system for production of photosynthetic microorganisms such as microalgae and cyanobacteria. In various embodiments, this system may include the use of extended surface area to reduce light intensity and increase photosynthetic efficiency, an external water basin to provide structure and thermal regulation at low cost, flexible plastic or composite panels that are joined together make triangular or other shapes in cross-section when partially submerged in water, use of positive gas buoyancy and pressure to maintain the structural integrity of the photobioreactor chambers and use of structure to optimize distribution of diffuse light. Other embodiments of Willson et al., concern air tubes comprised of plastic film at the bottom of each photobioreactor chamber to provide sparging air bubbles to the chamber. The photobioreactor system design also contains gas exchange, temperature control, air pumping, liquid pumping, filtration, media recycling and harvesting methods. For biofuels production, the photobioreactor system is said to include a separate growth photobioreactor and secondary stress reactor.

Hazelbeck et al., in US Published Patent Application No. 2009/0081743, provide a portable system and method for producing biofuel from algae. In the portable system, a chemostat and a plug flow reactor formed from plastic bladders are interconnected. Further, an algae separator is in fluid communication with the plug flow reactor for removing algae cells. Also, the system of Hazelbeck et al., includes a device for processing biofuel from the algae cells. The system includes a temperature controller to maintain desired temperatures in the chemostat and plug flow reactor for algae growth and intracellular algae production. To further support algae cell growth, the system includes a device for capturing carbon dioxide and delivering the carbon dioxide to the chemostat.

WO2007/098150 in the name of Hu et al. provides photobioreactors, modules thereof, and methods for use in culturing and harvesting algae and cyanobacteria. The photobioreactors of Hu et al. are constructed of a container adapted for holding fluid, which is made of opposing first and second sidewalls, wherein at least one of the first and second sidewalls is transparent; opposing first and second endwalls; a container bottom; and a container cover, wherein the first and second sidewalls has a plurality of separate sections, and wherein the separate sections are in fluid communication; support struts for connecting the plurality of separate sections of the first and second sidewalls; at least one inlet port in fluid communication with the container; at least one outlet port in fluid communication with the container; an aeration system in fluid communication with the container; and a temperature control system connected to the container so as to control temperature of fluid within the container.

Vermaas et al. in WO2008/051865 disclose a system and method for growing photosynthetic cells in conduit. The system and method supply light, $CO_2$ and nutrients to the cells. The system and method also dampen thermal variations in the conduit. The system of Vermaas et al. contains: at least one conduit having an outer surface, an inner surface, an inner volume, a length, and at least a portion that permits sunlight to pass into the inner volume during use, wherein at least a portion of the at least one conduit is exposed to sunlight during day; a thermal dampening system in operable relationship to the at least one conduit; a $CO_2$ supply system configured to supply $CO_2$ to the inner volume during use; a nutrient-supply system configured to supply nutrients to the inner volume during use; and a separation system configured to remove the photosynthetic cells from the at least one conduit during use.

WO2009/051478 in the name of Van De Ven et al., describes a photobioreactor for the production of phototropic organisms, especially (micro)algae. The reactor is made of at least a reactor component in which a mixture of a liquid and some phototropic organisms has been or is to be introduced, where the reactor component has one or more tubes whose walls are at least partly transparent in order to allow daylight to enter the reactor component to enable the organisms in it to carry out their photosynthesis, also having an inlet, connected to the reactor component, for introducing the liquid and/or the phototropic organisms, an outlet, connected to the reactor component, for removing the mixture of the liquid and the resulting phototropic organisms, as well as a cleaning system connected to the reactor component, for the mechanical cleaning of the inside surface of the tubes so that it can continue to allow sufficient daylight to enter for the photosynthesis. The cleaning system of Van De Ven et al. has a first cleaning station, which is mounted between the inlet and the reactor component, a second cleaning station, which is mounted between the reactor component and the outlet, a cleaning tool that can move to and fro between the cleaning stations, along the reactor component with the shape and size of the cleaning tool being adjusted according to the inside surface of the walls of the tubes of the reactor component in order to clean these walls by the movement of the cleaning tool.

Van De Ven et al., in WO2009/051479 detail a photobioreactor for the production of phototropic organisms, especially (micro)algae, where the reactor is constructed of at least a reactor component into which a mixture of a liquid and phototropic organisms has been or is to be introduced, with the reactor component having a reactor vessel and one or more tubes connected to the reactor vessel. The reactor vessel is essentially protected from daylight, and the tubes are at least partly transparent, so that daylight can penetrate the reactor component to enable the organisms to carry out their photosynthesis. One or more floats ensure buoyancy for at least the tubes of the reactor component when the bioreactor is placed in an expanse of water, especially a lake or the sea. Van De Ven et al. also provide a method for the production of phototropic organisms, especially (micro)algae, involving the provision of a photobioreactor; the introduction of a mixture of a liquid and phototropic organisms into the photobioreactor; the placement and floating of at least the transparent tubes of the bioreactor in an expanse of water, especially a lake or the sea; and growing the microorganisms under the influence of daylight entering the transparent tubes.

Thus, there continues to exist a need in the art for photobioreactors for algae growth (e.g. for biofuel generation) that are less expensive to set up and to operate than conventional pipe reactors and which give high algae yields.

SUMMARY OF THE INVENTION

Accordingly, the present invention provides such a photobioreactor. The inventive flow-through photobioreactor contains at least one thermoplastic multi-wall sheet having an upper layer and a lower layer having arranged there between at least two sidewalls, at least one inner wall and two or more end caps. Also provided is a process for the production of a biofuel with the inventive flow-through photobioreactor involving flowing an algae solution into a photobioreactor containing at least one thermoplastic multi-wall sheet having an upper layer and a lower layer having arranged there between at least two sidewalls, at least one inner wall and two or more end caps, exposing the algae solution to sunlight, harvesting oil from the algae and converting the oil to a biofuel.

The flow-through photobioreactor and process of the present invention have the following advantages: genetically engineered microbes that give higher yields cannot escape into the environment, water in the system does not evaporate, no weeding (presence of unwanted algae), UV light from the sun is filtered out by the reactor walls, temperature control is possible, and $CO_2$ from power plants, breweries, etc. can be artificially fed to increase yield. The inventive photobioreactor is also less expensive to build than pipe reactors and may have low energy costs to operate, because little or no energy is needed for agitation and pumping in a gravity assisted embodiment.

These and other advantages and benefits of the present invention will be apparent from the Detailed Description of the Invention herein below.

BRIEF DESCRIPTION OF THE FIGURES

The present invention will now be described for purposes of illustration and not limitation in conjunction with the figures, wherein.

DETAILED DESCRIPTION OF THE INVENTION

The present invention will now be described for purposes of illustration and not limitation. Except in the operating examples, or where otherwise indicated, all numbers expressing quantities, percentages, and so forth in the specification are to be understood as being modified in all instances by the term "about."

The present invention provides a flow-through photobioreactor containing at least one thermoplastic multi-wall sheet having an upper layer and a lower layer having arranged there between at least two sidewalls, at least one inner wall and two or more end caps.

The present invention further provides a process for the production of a biofuel involving flowing an algae solution into a flow-through photobioreactor containing at least one thermoplastic multi-wall sheet having an upper layer and a lower layer and having arranged there between at least two sidewalls, at least one inner wall and two or more end caps, exposing the algae solution to sunlight, harvesting the algae, drying the algae, extracting oil from the dried algae and converting the oil to a biofuel.

Figure 1:
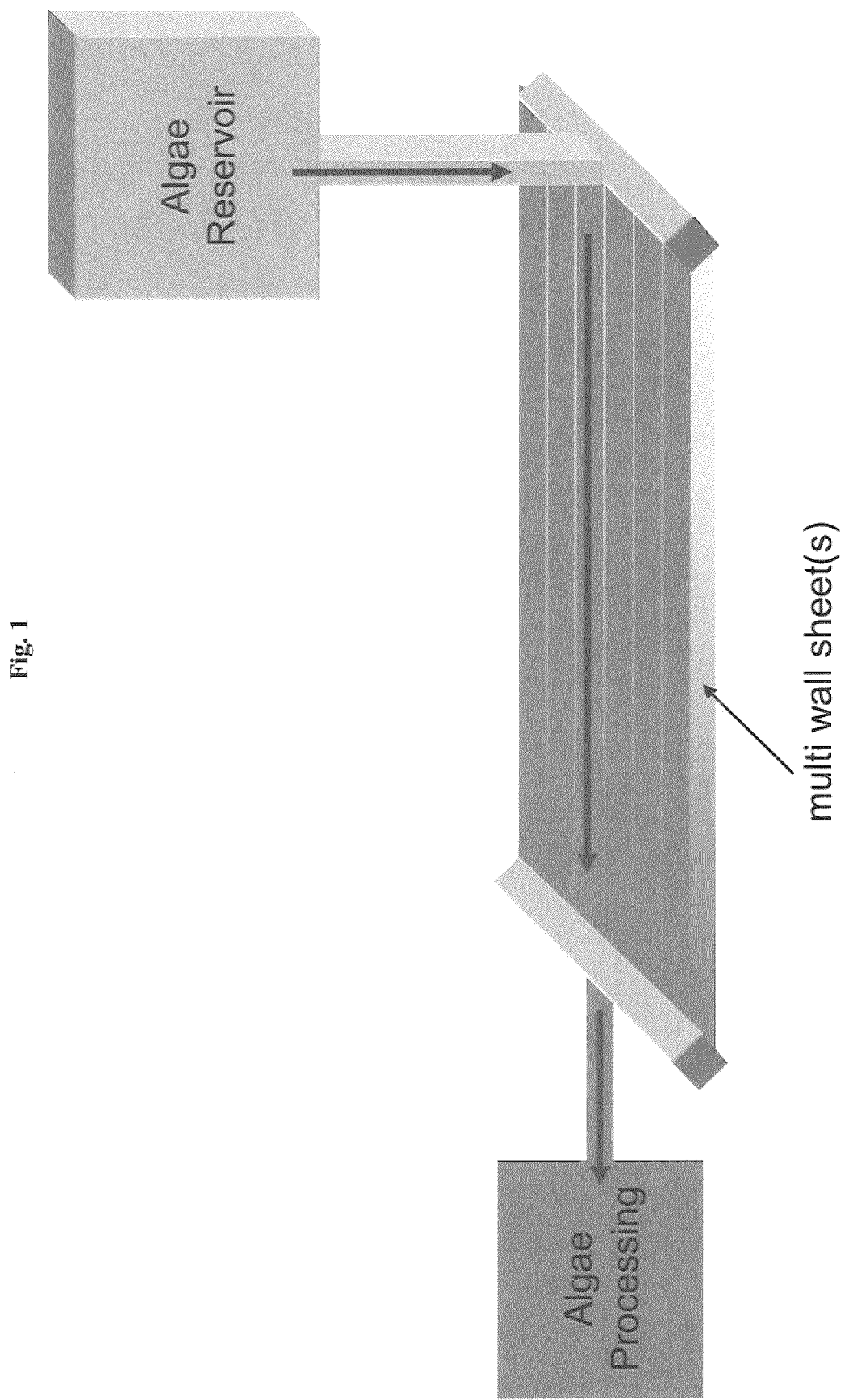
FIG. 1 shows one embodiment of the inventive flow-through thermoplastic multi-wall sheet photobioreactor.
Figure 3:
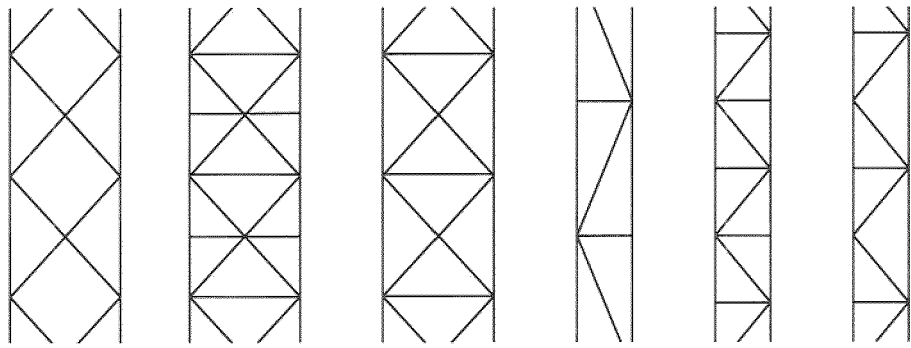
FIG. 3 provides additional cross-sectional views of configurations for the thermoplastic multi-wall sheets of the inventive flow-through photobioreactor.
Figure 2:
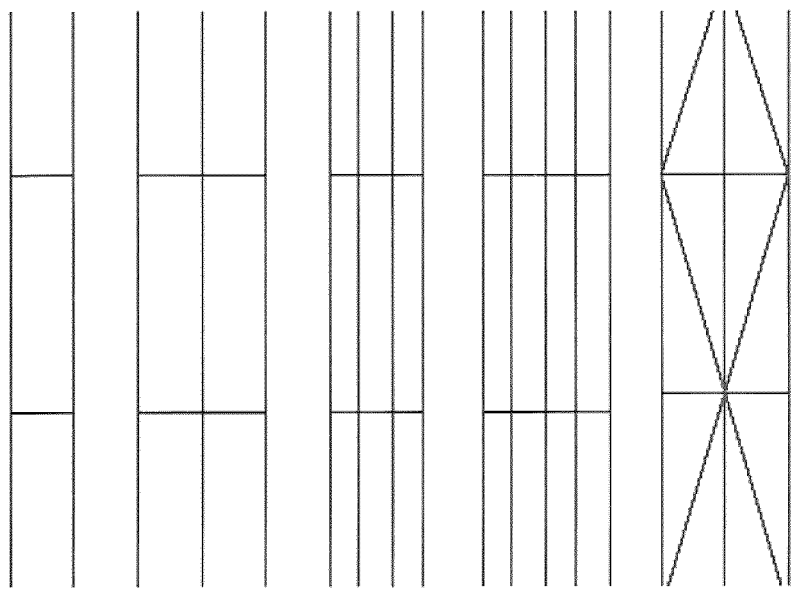
FIG. 2 illustrates cross-sectional views of several configurations for the thermoplastic multi-wall sheets of the inventive flow-through photobioreactor.

As can be appreciated by reference to FIG. 1, a microbe solution may preferably be fed into the flow-through photobioreactor of the present invention from an elevated reservoir. In this embodiment of the invention, the weight of the microbe solution pushes the solution through the thermoplastic multi-wall sheet ("MWS") having one, two, three or more inner walls. The inner walls may be oriented parallel, perpendicularly or diagonally relative to the upper and lower layers of the thermoplastic multi-wall sheet as is shown in FIGS. 2 and 3. Because this embodiment is gravity assisted, no energy is required to pump the solution as is the case in conventional pipe reactors. To further assist with flow, the photobioreactor may be placed on a downward slope. As those skilled in the art will appreciate, however, if the algae solution gets too thick or if the reactor is too long, the algae solution will require pumping.

The thermoplastic multi-wall sheets useful in the present invention are preferably made of a transparent or translucent plastic, such as polycarbonate ("PC"), co-polycarbonate ("co-PC"), polyestercarbonate, copolyestercarbonate, siloxane-polycarbonate, siloxane-copolycarbonate, polyester, co-polyester, polyvinyl chloride ("PVC"), co-polyvinyl chloride ("co-PVC"), polymethylmethacrylate ("PMMA"), co-polymethylmethacrylate ("co-PMMA"), polypropylene ("PP"), cyclic olefin copolymer ("COC"), fluoropolymers, thermoplastic olefin ("TPO"), styrene acrylonitrile ("SAN"), thermoplastic polyurethane ("TPU") or transparent or translucent blends of these materials.

The outer surface of the thermoplastic multi-wall sheet, on the side that is directed towards the sunlight, preferably has at least one outer cap layer attached thereto. This outer cap layer can be coextruded, laminated or painted and increases the weather resistance of the thermoplastic multi-wall sheets. The outer cap may be made of polycarbonate with a high UV absorber content or a co-polycarbonate, such as Lexan® SLX or polymethylmethacrylate. It may also be a UV-stabilized clearcoat on an acrylic base or a urethane base or a siloxane hardcoat, etc.

The thermoplastic multi-wall sheet of the inventive photobioreactor preferably has a light transmission of greater than 60%, more preferably greater than 70%, and most preferably greater than 80%. The outer surface of the upper layer of the thermoplastic multi-wall sheet, which faces the sun, preferably has a light transmission of greater than 70%, more preferably greater than 80%, even more preferably greater than 85%, and most preferably greater than 87%. The underside (i.e., the outer surface of the lower layer) of the thermoplastic multi-wall sheet may have a coextruded or coated layer that reflects light, such as a silver layer or a layer that selectively reflects certain wavelengths (e.g. dark or light red and/or blue). The underside of the thermoplastic multi-wall sheet may also have a coextruded or coated layer with abrasion resistance.

The inner surface of the thermoplastic multi-wall sheet may contain at least one inner cap layer. The function of this inner cap layer may be to enhance the chemical resistance and/or to lower the algae adhesion. Useful materials for the inner cap layer include co-polycarbonate, polyester, co-polyester, polyvinyl chloride, co-polyvinyl chloride, polymethylmethacrylate, co-polymethylmethacrylate, polypropylene, cyclic olefin copolymer, fluoropolymers, thermoplastic olefin, styrene acrylonitrile, thermoplastic polyurethane or transparent or translucent blends of these materials or paints (clearcoats).

Instead of cap layers, it is also possible to infuse additives into the thermoplastic multi-wall sheet to enhance the UV stability, chemical resistance, and/or to decrease the algae adhesion. These additives can be e.g. UV absorbers for the outside and anti microbial additives to lower the algae adhesion. Such infusion techniques are known to those skilled in the art.

Figure 4:
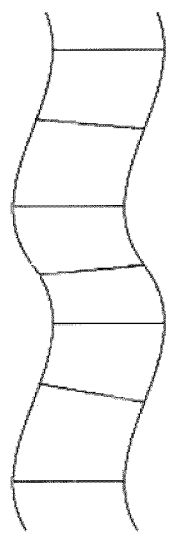
FIG. 4 depicts a corrugated thermoplastic multi-wall sheet useful in the inventive flow-through photobioreactor.

The inner walls of the thermoplastic multi-wall sheet may be arranged in various configurations such as those shown in FIGS. 2 and 3. Corrugated multi wall sheets, such as illustrated in FIG. 4 may also prove useful in the present invention.

There are other configurations that may be used, depending on the needs of the photobioreactor user. The configurations, shapes and the thickness of the thermoplastic multi-wall sheet depend on the speed that the microbe solution flows through the thermoplastic multi-wall sheet and the desired residence time. These parameters will also determine the wall thicknesses to be used. The thickness will also depend on how dense the microbe solution is. In the beginning of the growth process (i.e., the right side of FIG. 1), there are not too many microbes. The farther down the photobioreactor the solution flows (i.e., to the left side of FIG. 1); the more microbes grow and absorb light. It may be necessary to have lower thermoplastic multi-wall sheet thicknesses or to have different profiles. The thermoplastic multi-wall sheets preferably have a thickness of 1 inch to 10 inches, more preferably 2 inches to 9 inches, even more preferably 3 inches to 7 inches, and most preferably 4 inches to 6 inches. The thermoplastic multi-wall sheets in the present invention may have a thickness in an amount ranging between any combination of these values, inclusive of the recited values.

The thermoplastic multi-wall sheets may be made in one long piece or multiple thermoplastic multi-wall sheets may be placed in line. Where placed in line, the thermoplastic multi-wall sheets can either be connected through connector pieces or glued or welded together. When gluing or welding the thermoplastic multi-wall sheets together, it is important to at least bond the outer walls firmly together so that no microbe solution can escape. The inner walls may or may not be bonded to each other. The ends of the multiwall sheet have end caps to prevent the outflow of material during the algal growth process. The end caps may preferably be funnel shaped to facilitate the rapid transfer of material into and out of the photobioreactor before and after the growth cycle.

To compensate for thermal expansion and contraction, it is preferred to use connector pieces. Connector pieces that fit over the thermoplastic multi-wall sheets allow for the sheets to be connected water tight, but without the thermoplastic multi-wall sheets touching each other. The connector pieces are also preferred locations for taking measurements of the parameters, like $CO_2$ content, nutrient content, pH value etc., that help steer the process and are preferred locations to feed nutrients, air and/or $CO_2$, and make pH adjustments, etc. Otherwise, measurement and feeding may be done directly into the chambers of the thermoplastic multi-wall sheet.

Figure 5:
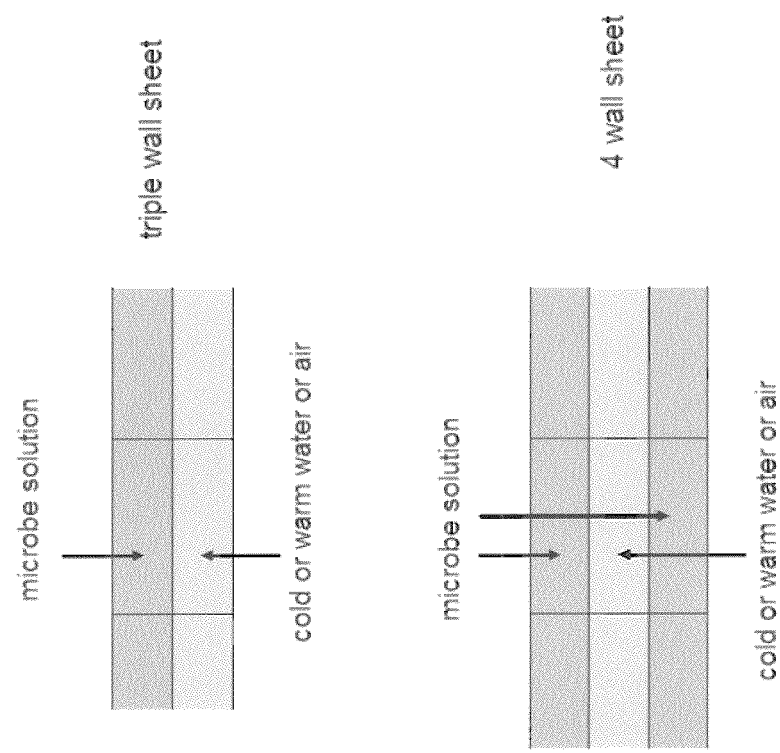
FIG. 5 shows cross sectional views of 3-wall and 4-wall configurations of the thermoplastic multi-wall sheets for heating or cooling the inventive flow-through photobioreactor.
Figure 6:
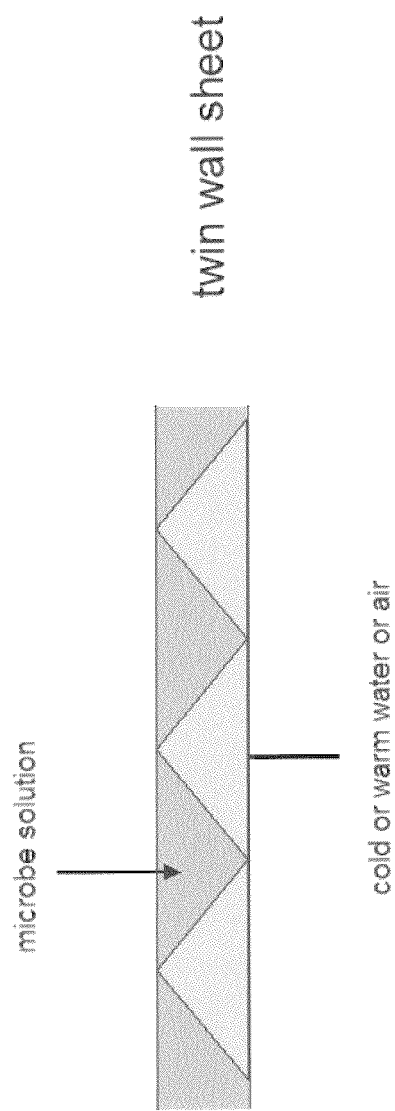
FIG. 6 shows a cross sectional view of the configuration of a twin wall sheet in which the inner walls are arranged diagonally relative to the upper and lower layers of the thermoplastic multi-wall sheets of the inventive flow-through photobioreactor.
Figure 7:
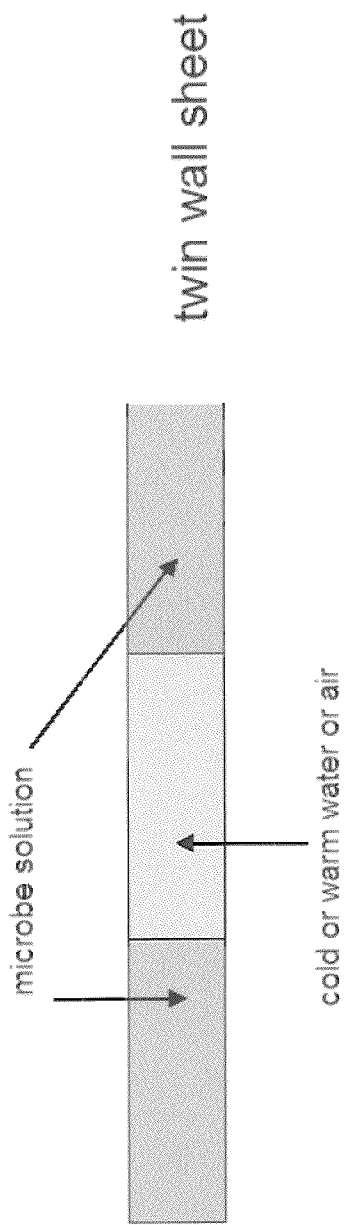
FIG. 7 shows a cross sectional view of another configuration of the thermoplastic multi-wall sheets for heating or cooling the inventive flow-through photobioreactor.

Heating or cooling can be accomplished by flowing hot or cold air or water in the chambers formed by the inner and outer walls as illustrated in FIGS. 5-7.

As shown in cross section in the upper portion of FIG. 5 for a triple wall sheet, the algal solution flows in a first set of chambers formed between the upper layer of the thermoplastic multi-wall sheet, the inner walls and sidewalls. Heating or cooling air or water flows in a second set of chambers formed between the lower layer of the thermoplastic multi-wall sheet, the inner walls and sidewalls.

As illustrated in cross section in the lower portion of FIG. 5 for a 4-wall sheet, the algal solution flows in the upper and lower chambers with heating or cooling air or water flowing through the middle chambers.

FIG. 6 provides a cross sectional view of a twin wall sheet with inner walls arranged diagonally with respect to the upper and lower layers of the sheet. The microbe solution flows in the upper chambers formed between the upper layer and two inner diagonal walls. The heating or cooling air or water flows in the lower chambers formed between the lower layer and the two inner diagonal walls.

FIG. 7 shows a cross sectional view of another configuration of the present invention in which the microbe solution flows in the outer chambers and the heating or cooling air or water flows in the middle chamber.

At the end of the thermoplastic multi-wall sheet line, the microbe solution may be collected via the end caps for further processing and conversion into biofuel. Such conversion may take place by flowing an algae solution into the photobioreactor, exposing the algae solution to sunlight, harvesting the algae, drying the algae, extracting oil from the dried algae and converting the oil to a biofuel. Those skilled in the art are aware of processes and techniques for harvesting the oil and for converting it to a fuel.

The photobioreactor of the present invention may be used to produce a variety of biofuels such as biodiesel, bioethanol, biogasoline, biomethanol and biobutanol.

The foregoing description of the present invention is offered for the purpose of illustration and not limitation. It will be apparent to those skilled in the art that the embodiments described herein may be modified or revised in various ways without departing from the spirit and scope of the invention. The scope of the invention is to be measured by the appended claims.

What is claimed is:

1. A flow-through photobioreactor comprising at least one thermoplastic multi-wall sheet having an upper layer and a lower layer having arranged there between at least two sidewalls, at least one inner wall, two or more end caps, and an algae reservoir positioned above the thermoplastic multi-wall sheet to permit algae flow into the thermoplastic multi-wall sheet, wherein the upper layer and the lower layer are each made of one material independently selected from the group consisting of transparent or translucent polycarbonate, co-polycarbonate, polyestercarbonate, copolyestercarbonate, siloxane-polycarbonate, siloxane-copolycarbonate, polyester, co-polyester, polyvinyl chloride, co-polyvinyl chloride, polymethylmethacrylate, co-polymethylmethacrylate, polypropylene, cyclic olefin copolymer, fluoropolymers, thermoplastic olefin, styrene acrylonitrile, thermoplastic polyurethane and transparent or translucent blends thereof and wherein an outer surface of the thermoplastic multi-wall sheet has applied thereto one or more outer cap layers.

2. The flow-through photobioreactor according to claim, 1, wherein the outer cap layer is coextruded, laminated or painted to the outer surface of the thermoplastic multi-wall sheet.

3. The flow-through photobioreactor according to claim 1, wherein an inner surface of the thermoplastic multi-wall sheet has applied thereto one or more inner cap layers.

4. The flow-through photobioreactor according to claim 3, wherein the inner cap layer is made of a member selected from the group consisting of co-polycarbonate, polyester, co-polyester, polyvinyl chloride, co-polyvinyl chloride, polymethylmethacrylate, co-polymethylmethacrylate, polypropylene, cyclic olefin copolymer, fluoropolymers, thermoplastic olefin, styrene acrylonitrile, thermoplastic polyurethane, transparent or translucent blends thereof and clearcoats.

5. The flow-through photobioreactor according to claim 1, wherein the thermoplastic multi-wall sheet has two or more inner walls.

6. The flow-through photobioreactor according to claim 1, wherein the at least one inner wall is arranged parallel relative to the upper and lower layers.

7. The flow-through photobioreactor according to claim 1, wherein the at least one inner wall is arranged perpendicularly relative to the upper and lower layers.

8. The flow-through photobioreactor according to claim 1, wherein the at least one inner wall is arranged diagonally relative to the upper and lower layers.

9. The flow-through photobioreactor according to claim 5, wherein the two or more inner walls are independently arranged in one or more of parallel, perpendicularly and diagonally relative to the upper and lower layers.

10. The flow-through photobioreactor according to claim 1, wherein the upper layer of the thermoplastic multi-wall sheet has a light transmission of greater than 70%.

11. The flow-through photobioreactor according to claim 1, wherein the upper layer of the thermoplastic multi-wall sheet has a light transmission of greater than 80%.

12. The flow-through photobioreactor according to claim 1, wherein the upper layer of the thermoplastic multi-wall sheet has a light transmission of greater than 85%.

13. The flow-through photobioreactor according to claim 1, wherein the upper layer of the thermoplastic multi-wall sheet has a light transmission of greater than 87%.

14. The flow-through photobioreactor according to claim 1, wherein the thermoplastic multi-wall sheet has a thickness of from about 1 inch to about 10 inches.

15. The flow-through photobioreactor according to claim 1, wherein the thermoplastic multi-wall sheet has a thickness of from about 2 inches to about 9 inches.

16. The flow-through photobioreactor according to claim 1, wherein the thermoplastic multi-wall sheet has a thickness of from about 3 inches to about 7 inches.

17. The flow-through photobioreactor according to claim 1, wherein the thermoplastic multi-wall sheet has a thickness of from about 4 inches to about 6 inches.

18. A process for the production of a biofuel comprising:
flowing an algae solution into a flow-through photobioreactor comprising at least one thermoplastic multi-wall sheet having an upper layer and a lower layer and having arranged there between at least two sidewalls, at least one inner wall, two or more end caps and an algae reservoir positioned above the thermoplastic multi-wall sheet to permit algae flow into the thermoplastic multi-wall sheet,
wherein the upper layer and the lower layer are each made of one material independently selected from the group consisting of transparent or translucent polycarbonate, co-polycarbonate, polyestercarbonate, copolyestercarbonate, siloxane-polycarbonate, siloxane-copolycarhonate, polyester, co-polyester, polyvinyl chloride, co-polyvinyl chloride, polymethylmethacrylate, co-polymethylmethacrylate, polypropylene, cyclic olefin copolymer, fluoropolymers, thermoplastic olefin, styrene acrylonitrile, thermoplastic polyurethane and transparent or translucent blends thereof and wherein an outer surface of the thermoplastic multi-wall sheet has applied thereto one or more outer cap layers;
exposing the algae solution to sunlight;
harvesting the algae;
drying the algae;
extracting oil from the dried algae; and
converting the oil to a biofuel.

19. The process according to claim 18, wherein the biofuel is selected from the group consisting of biodiesel, bioethanol, biogasoline, biomethanol, and biobutahol.

* * * * *